United States Patent [19]

Gerolymatos

[11] Patent Number: 6,001,852
[45] Date of Patent: Dec. 14, 1999

[54] CLIOQUINOL FOR THE TREATMENT OF ALZHEIMER'S DISEASE

[75] Inventor: Panayotis N. Gerolymatos, Kryoneri Attikis, Greece

[73] Assignee: P.N. Gerolymatos S.A., Kryoneri Attikis, Greece

[21] Appl. No.: 09/023,544

[22] Filed: Feb. 13, 1998

Related U.S. Application Data

[63] Continuation-in-part of application No. PCT/IB97/00983, Aug. 8, 1997.

[30] Foreign Application Priority Data

Aug. 13, 1996 [GR] Greece ............................... 960100286

[51] Int. Cl.$^6$ .......................... A61K 31/70; A61K 31/47
[52] U.S. Cl. .............................................. 514/311; 514/52
[58] Field of Search ......................................... 514/311, 52

[56] References Cited

U.S. PATENT DOCUMENTS

| | | | |
|---|---|---|---|
| 3,574,819 | 4/1971 | Gross et al. | 424/21 |
| 5,286,492 | 2/1994 | Dettmar et al. | 424/449 |
| 5,373,021 | 12/1994 | Marangos | 514/483 |
| 5,505,958 | 4/1996 | Bello et al. | 424/448 |
| 5,607,691 | 3/1997 | Hale et al. | 424/449 |

FOREIGN PATENT DOCUMENTS

| | | |
|---|---|---|
| 3932338 | 4/1991 | Germany . |
| WO 92/18111 | 10/1992 | WIPO . |
| WO 93/10459 | 5/1993 | WIPO . |
| WO 95/19178 | 7/1995 | WIPO . |
| WO 95/31199 | 11/1995 | WIPO . |

OTHER PUBLICATIONS

"Idiosyncratic Neurotoxicity: Clioquinol and Bismuth," 1980, *The Lancet* p.857–858.

Baumgartner et al., 1979, Neurotoxicity of halogenated hydroxyquinolines: clinical analysis of cases reported outside Japan, *Journal of Neurology, Neurosurgery, and Psychiatry* 42:1073:1083.

Beppu, H., 1973, "Toxicity of Clioquinol (5–chloro–7–iodo—8–hydroxy quinoline) on chick embryo dorsal root ganglia in tissue culture," 13:551–560 (w/English abstract).

Borg–Neczak et al., 1994, "Effect of 8–Hydroxy–,8–Mercapto– and 5–Chlorol–7–iodo–8–hydroxy–quinoline on the Uptake and Distribution of Nickel in Mice," *Pharmacology & Toxicology* 74:185–192.

Bush et al., 1994, "Rapid Induction of Alzheimer Aβ Amyloid Formation by Zinc," *Science* 265:1464–1467.

Bush et al., 1995, "The Role of Zinc in the Cerebral Deposition of Aβ Amyloid in Alzheimer's Disease," *Amyloidogenesis* pp. 607–618.

Bush et al., 1995, "Zinc and Alzheimer's Disease," *Science* 268:1921–1923.

Chaiyabutr et al., 1985, "Urinary Bladder Effects After Oral Dosages of the ntidiarrhoeal Drug (Clioquinol/Phanquinone/Oxyphenonium Bromide) in Experimental Drugs," *J. Med. Ass. Thailand* 68(12):649–653.

Committee on Drugs, "Blindness and Neuropathy From Diiodohydroxyquin–Like Drugs," American Academy of Pediatrics, pp.378–379 (1990).

Crapper McLachlan et al., 1991, Intramuscular desferrioxamine in patients with Alzheimer's disease, *The Lancet* 337:1304–1308.

Degen et al., 1979, "Precutaneous Absorption of Clioquinol (Vioform®)," *Dermatologica* 159:295–301.

Esler et al., 1996, "Zinc–Induced Aggregation of Human and Rat β–Amyloid Peptides in Vitro," *Journal of Neurochemistry* 66(2):723–732.

Fitzgerald, 1995, "Zinc and Alhzeimer's Disease," *Science* 268:1920–1923.

Goto et al., 1982, "Impairment of Visual System of Beagles Orally Ingesting Clioquinol," *The Journal of Toxicological Sciences* 7:19–25.

Goto et al., 1982, "Deterioration of Spinal Reflex in Beagles Orally Ingesting Clioquinol," *The Journal of Toxicological Sciences* 7:–12.

Holtzman et al., 1996, "Developmental abnormalities and age–related neurodegeneration in a mouse model on Down syndrome," *Proc. Natl. Acad. Sci. USA* 93:13333–13338.

Hori et al., 1987, "5–Chloro–7–lodo–8–Hydroxyquinoline (Clioquinol) Inhibits The Nerve Growth Factor–Induced Stimulation Of RNA Synthesis In Neonatal Rat Superior Cervical Ganglion, In Vitro," *The Journal of Toxicological Sciences* 12:97–109.

Jack et al., 1973, "Pharmacokinetics of Iodochlorhydroxyquin in Man," *Journal of Pharmaceutical Sciences* 62(12):1929–1932.

Kaiser, 1994, "Alzheimer's: Could Thre Be a Zinc Link?," *Science* 265:1365.

Kawahara et al., 1997, "Alzheimer's Disease Amyloid β–Protein Forms $Zn^{2+}$–Sensitive, Cation–Selective Channels Across Excised Membrane Patches from Hypothalamic Neurons," *Biophysical Journal* 73:67–75.

Kirschner et al., 1987, "Synthetic peptide homologous to α protein from Alzheimer disease forms amyloid–like fibrils in vitro," *Proc. Natl. Acad. Sci. USA* 84:6953–6957.

Kono, R., 1975, "Introductory Review Of Subacute Myelo–Optico–Neuropathy (SMON) And Its Studies Done By The SMON Research Commission," *Japan J. Med. Sci. Biol.* 28:1–21.

(List continued on next page.)

*Primary Examiner*—Theodore J. Criares
*Attorney, Agent, or Firm*—Pennie & Edmonds LLP

[57] ABSTRACT

A new pharmaceutical composition is disclosed that comprises clioquinol, vitamin $B_{12}$, and, optionally, pharmaceutical acceptable carriers and/or excipients. The use of the pharmaceutical composition removes or alleviates the side effects of clioquinol.

40 Claims, 2 Drawing Sheets

OTHER PUBLICATIONS

Kotaki et al., 1983, "Intestinal Absorption and Metagolism of Clioquinol in the Rat," *J. Pharm. Dyn.* 6:881–887.

Koyama ete al., 1989, "Electrophysiological changes in the fasciculus gracilus of the cat following chronic clioquinol administration," *Journal of the Neurological Sciences* 94:271–282.

LaFerla et al., 1996, "Extracellular Deposition of β–Amyloid upon p53–dependent Neuronal Cell Death in Transgenic Mice," *J. Clin. Ivest.* 98(7):1626–1632.

Meade, T.W., 1975, "Subacute myelo–optic neuropathy and clioquinol," *Brit. J. prev. soc. Med.* 29:157–169.

Mumenthaler et al., 1979, "Transient global amnesia after clioquinol," *Journal of Neurology, Neurosurgery, and Psychiatry* 42:1084–1090.

Muratov et al., 1983, "Interaction of Voltaren and some Pyrazolone and Aniline Derivatives with Endoperoxide Prostaglandin Synthetase," pp. 44–46 (w/English abstract).

Nakae et al., 1972, "Relation between Subacute Myelooptic Neuropathy (S.M.O.N.) and Clioquinol: Nationwide Survey," *The Lancet* pp. 171–173.

Oakley, Jr., G.P., 1973, "The Neurotoxicity of the Halogenated Hydroxyquinolines," *JAMA* 225:(4):395–397.

Oguro, 1974, "The interference of the water–soluble organic compounds in atomic absorption spectrophotometry of calcium," *Japan Analyst* pp.1375–1378.

Okada et al., 1984, "Effects Of Metal–Containing Drugs Taken Simultaneously With Clioquinol Upon Clinical Features Of SMON," *The Journal of Toxicological Sciences* 9:327–341.

O'Mahony et al., 1995, "Bone Aluminium Content in Alzheimer's Disease," *Dementia* 6:69–72.

Ozawa et al., 1986, "Experimental Clioquinol Intoxication in Rats: Abnormalities in Optic Nerves and Small Nerve Cells of Dorsal Root Ganglia," *Acta Neuropathol (Berl)* 69:272–277.

Pericin, 1979, "Comparison of the Acute Toxicity of Clioquinol, Histamine, and Chloroform in Different Strains of Mice," *Arch. Toxicol.* Supple. 2:371–373.

Polites, 1996, "Transgenic model application to drug discovery," *Int. J. Exp. Path.* 77:257–262.

Ricoy et al., 1982, "Subacute Myelo–Optic Neuropathy (SMON)," *Journal of the Neurological Sciences* 53:241–251.

Ross et al., 1997, "Zinc alters conformation and inhibits biological activities of nerve growth factor and related neurotrophins," *Nature Medicine* 3(8):872–878.

Sargeaunt et al., 1976, "In vitro sensitivity of *Entamoeba histolytica* to furazolidone and iodochlorhydroxyquin, separate and combined," *Transactions of the Royal Society of Tropical Medicine and Hygiene* 70(1):54–56.

Schmid et al., 1973, "Studies of the Distribution and Excretion of Clioquinol in the Animal," *Arzneim.–Forsch. (Drug Res.)* 23(11):1560–1566.

Shigematsu, I., 1975, "Subacute Myelo–Optico–Neuropathy (SMON) And Clioquinol," p.35–54.

Shiraki, H., 1972, "The Neuropathology Of Subacute Myelo–Optico–Neuropathy, "SMON", In The Humans," pp. 101–164.

Sobue et al., 1971, "Myeloneuropathy with abdominal disorders in Japan," *Neurology* 21:168–173.

Sobue, "Clinical aspects of subacute myelo–optico–neuropathy (SMON)," *Handbook of Clinical Neurology* 37:116–139 (1985).

Tamura et al., 1973, "Identification Of Green Pigment And Analysis Of Clioquinol In Specimens From Patients With Subacute Myelo–Optico–Neuropathy," *Clinica Chimica Acta* 47:13–20.

Tamura, Z., 1975, "Clinical Chemistry of Clioquinol," pp.69–77.

Tateishi et al., 1975, "Experimental Reproduction of SMON in Animals by Prolonged Administration of Clioquinol: Clinoco–Pathological Findings," 28:165–186.

Tateishi et al., 1976, "Neurotoxicity of Iodoxyquinoline: A Further Study on Beagle Dogs," 28:187–195.

Thomas et al., 1984, "Correlated Nerve Conduction, Somatosensory Evoked Potential And Neuropathological Studies In Clioquinol And 2,5–Hexanedione Neurotoxicity In The Baboon," *Journal of the Neurological Sciences* 64:277–295.

Tsubaki et al., 1971, "Neurological Syndrome Associated with Clioquinol," *The Lancet* 696–697.

Wadia, 1984, "SMON as seen from Bombay," *Acta Neurol Scand* 70(suppl 100): 159–164.

Weathersbee, A.A., 1943, "Observations On The Relative Attractiveness Of Man And Horse For Anopheles Albimanus Weideman," *The American Journal of Tropical Medicine* 14:25–33.

Weismann et al., 1978, "Effects of Penicillamine and Hydroxyquinoline on Absorption of Orally Ingested $^{65}$Zinc in the Rat," *The Journal of Investigative Dermatology* 71:242–244.

Wieniewski et al., 1996, "Some neuropathological aspects of Alzheimer's disease and its relevance to other disciplines," *Neuropathology and Applied Neurobiology* 22:3–11.

Wokes et al., 1955, "Human Dietary Deficiency of Vitamin $B_{12}$," *The American Journal of Clinical Mutrition* 3(5):375–382.

Yamanaka et al., 1973, "Uncoupling of Oxidative Phosphorylation of Rat Liver Mitochondria by Chinoform," *J. Biochem.* 73:993–998.

Yoshimura et al., 1992, "The Same Chemicals Induce Different Neurotoxicity When Administered in High Doses for Short Term or Low Doses for Long Term to Rats and Dogs," *Molecular and Chemical Neuropathology* 16:59–84.

Zaks et al., "Spasmolytic and Anti–Inflammatory Activity of 8–Hydroxyquinolines," p. 47 (English abstract).

Esler et al., 1996, "Zinc–Induced Aggregation of Human and Rat β–Amyloid Peptides in Vitro," *Jounral of Neurochemistry* 66(2):723–732.

Fitzgerald, 1995, "Zinc and Alhzeimer's Disease," *Science* 268:1920–1923.

Goto et al., 1982, "Impairment of Visual System of Beagles Orally Ingesting Clioquinol," *The Journal of Toxicological Sciences* 7:19–25.

Goto et al., 1982, "Deterioration of Spinal Reflex in Beagles Orally Ingesting Clioquinol," *The Journal of Toxicological Sciences* 7:–12.

Holtzman et al., 1996, "Developmental abnormalities and age–related neurodegeneration in a mouse model on Down syndrome," *Proc. Natl. Acad. Sci. USA* 93:13333–13338.

Hori et al., 1987, "5–Chloro–7–Iodo–8–Hydroxyquinoline (Clioquinol) Inhibits The Nerve Growth Factor Induces Stimulation Of RNA Synthesis In Neonatal Rat Superior Cervical Ganglion, In Vitro," *The Journal of Toxicological Sciences* 12:97–109.

Jack et al., 1973, "Pharmacokinetics of Iodochlorhydroxyquin in Man," *Journal of Pharmaceutical Sciences* 62(12):1929–1932.

Kaiser, 1994, "Alzheimer's: Could Thre Be A Zinc Link?," *Science* 265:1365.

Kawahara et al., 1997, "Alzheimer's Disease Amyloid β–Protein Forms $Zn^{2+}$–Sensitive, Cation–Selective Channels Across Excised Membrane Patches from Hypothalamic Neurons," *Biophysical Journal* 73:67–75.

Kirschner et al., 1987, "Synthetic peptide homologous to β protein from Alzheimer disease forms amyloid–like fibrils in vitro," *Proc. Natl. Acad. Sci. USA* 84:6953–6957.

Kono, R., 1975, "Introductory Review of Subacute Myelo–Optico–Neuropathy (SMON) And Its Studies Done By The SMON Research Commission," *Japan J. Med. Sci. Biol.* 28:1–21.

Kotaki et al., 1983, "Intestinal Absorption and Metagolism of Clioquinol in the Rat," *J. Pharm. Dyn.* 6:881–887.

Koyama ete al., 1989, "Electrophysiological changes in the fasciculus gracilis of the cat following chronic clioquinol administration," *Journal of the Neurological Sciences* 94:271–282.

LaFerla et al., 1996, "Extracellular Deposition of β–Amyloid upon p53–dependent Neuronal Cell Death in Transgenic Mice," *J. Clin. Invest.* 98(7):1626–1632.

Meade, T.W., 1975, "Subacute myelo–optic neuropathy and clioquinol," *Brit. J. prev. soc. Med.* 29:157–169.

Mumenthaler et al., 1979, "Transient global amnesia after clioquinol," *Journal of Neurology, Neurosurgery, and Psychiatry* 42:1084–1090.

Muratov et al., 1983, "Interaction of Voltaren and some Pyrazolone and Aniline Derivatives with Endoperoxide Prostaglandin Synthetase," pp. 44–46 (w/English abstract).

Nakae et al., 1972, "Relation between Subacute Myelooptic Neuropathy (S.M.O.N.) and Clioquinol: Nationwide Survey," *The Lancet* pp. 171–173.

Oakley, Jr., G.P., 1973, "The Neurotoxicity of the Halogenated Hydroxyquinolines," *JAMA* 225(4):395–397.

Oguro, 1974, "The interference of the water–soluble organic compounds in atomic absorption spectrophotometry of calcium," *Japan Analyst* pp. 1375–1378.

Okada et al., 1984, "Effects Of Metal–Containing Drugs Taken Simultaneously With Clioquinol Upon Clinical Features Of SMON," *The Journal of Toxicological Sciences* 9:327–341.

O'Mahony et al., 1995, "Bone Aluminium Content in Alzheimer's Disease," *Dementia* 6:69–72.

Ozawa et al., 1986, "Experimental Clioquinol Intoxication in Rats: Abnormalities in Optic Nerves and Small Nerve Cells of Dorsal Root Ganglia," *Acta Neuropathol (Berl)* 69:272–277.

Pericin, 1979, "Comparison of the Acute Toxicity of Clioquinol, Histamine, and Chloroform in Differen Strains of Mice," *Arch. Toxicol. Supple.* 2:371–373.

Polites, 1996, "Transgenic model applications to drug discovery," *Int. J. Exp. Path.* 77:257–262.

Ricoy et al., 1982, "Subacute Myelo–Optic Neuropathy (SMON)," *Journal of the Neurological Sciences* 53:241–251.

Ross et al., 1997, "Zinc alters conformation and inhibits biological activities of nerve growth factor and related neurotrophins," *Nature Medicine* 3(8):872–878.

Sargeaunt et al., 1976, "In vitro sensitivity of *Entamoeba histolytica* to furazolidone and iodochlorhydroxyquin, separate and combined," *Transactions of the Royal Society of Tropical Medicine and Hygiene* 70(1):54–56.

Schmid et al., 1973, "Studies of the Distribution and Excretion of Clioquinol in the Animal," *Arzneim.–Forsch. (Drug Res.)* 23(11):1560–1566.

Shigematsu, I., 1975, "Subacute Myelo–Optico–Neuropathy (SMON) And Clioquinol," pp. 35–54.

Shiraki, H., 1972, "The Neuropathology Of Subacute Myelo–Optico–Neuropathy, "SMON", In The Humans," pp. 101–164.

Sobue et al., 1971, "Myeloneuropathy with abdominal disorders in Japan," *Neurology* 21:168–173.

Sobue, "Clinical aspects of subacute myelo–optico–neuropathy (SMON)," *Handbook of Clinical Neurology* 37:116–139.

Tamura et al., 1973, "Identification Of Green Pigment And Analysis Of Clioquinol In Specimens From Patients With Subacute Myelo–Optico–Neuropathy," *Clinica Chimica Acta* 47:13–20.

Tamura, Z., 1975, "Clinical Chemistry of Clioquinol," p. 69–77.

Tateishi et al., 1975, "Experimental Reproduction of SMON in Animals by Prolonged Administration of Clioquinol: Clinoco–Pathological Findings," 28:165–186.

Tateishi et al., 1976, "Neurotoxicity of Iodoxyquinoline: A Further Study on Beagle Dogs," 28:187–195.

Thomas et al., 1984, "Correlated Nerve Conduction Somatosensory Evoked Potential And Neuropathological Studies In Clioquinol And 2,5–Hexanedione Neurotoxicity In The Baboon," *Journal of the Neurological Sciences* 64:277–295.

Tsubaki et al, 1971, "Neurological Syndrome Associated with Clioquinol," *The Lancet* 696–697.

Wadia, 1984, "SMON as seen from Bombay," *Acta Neurol Scand* 70(suppl 100):159–164.

Weathersbee, A.A., 1943, "Observations On The Relative Attractiveness Of Man And Horse For Anopheles Albimanus Weideman," *The American Journal of Tropical Medicine* 14:25–33.

Weismann et al., 1978, "Effects of Penicillamine and Hydroxyquinoline on Absorption of Orally Ingested $^{65}$Zinc in the Rat," *The Journal of Investigative Dermatology* 71:242–244.

Wieniewski et al., 1996, "Some neuropathological aspects of Alzheimer's disease and its relevance to other disciplines," *Neuropathology and Applied Neurobiology* 22:3–11.

Wokes et al., 1955, "Human Dietary Deficiency of Vitamin $B_{12}$," *The American Journal of Clinical Mutrition* 3(5):375–382.

Yamanaka et al., 1973, "Uncoupling of Oxidative Phosphorylation of Rat Liver Mitochondria by Chinoform," *J. Biochem.* 73:993–998.

Yoshimura et al., 1992, "The Same Chemicals Induce Different Neurotoxicity When Administered in High Doses for Short Term or Low Doses for Long Term to Rats and Dogs," *Molecular and Chemical Neuropathology* 16:59–84.

Zaks et al., "Spasmolytic and Anti–Inflammatory Activity of 8–Hydroxyquinolines," p. 47 (English abstract) (1980).

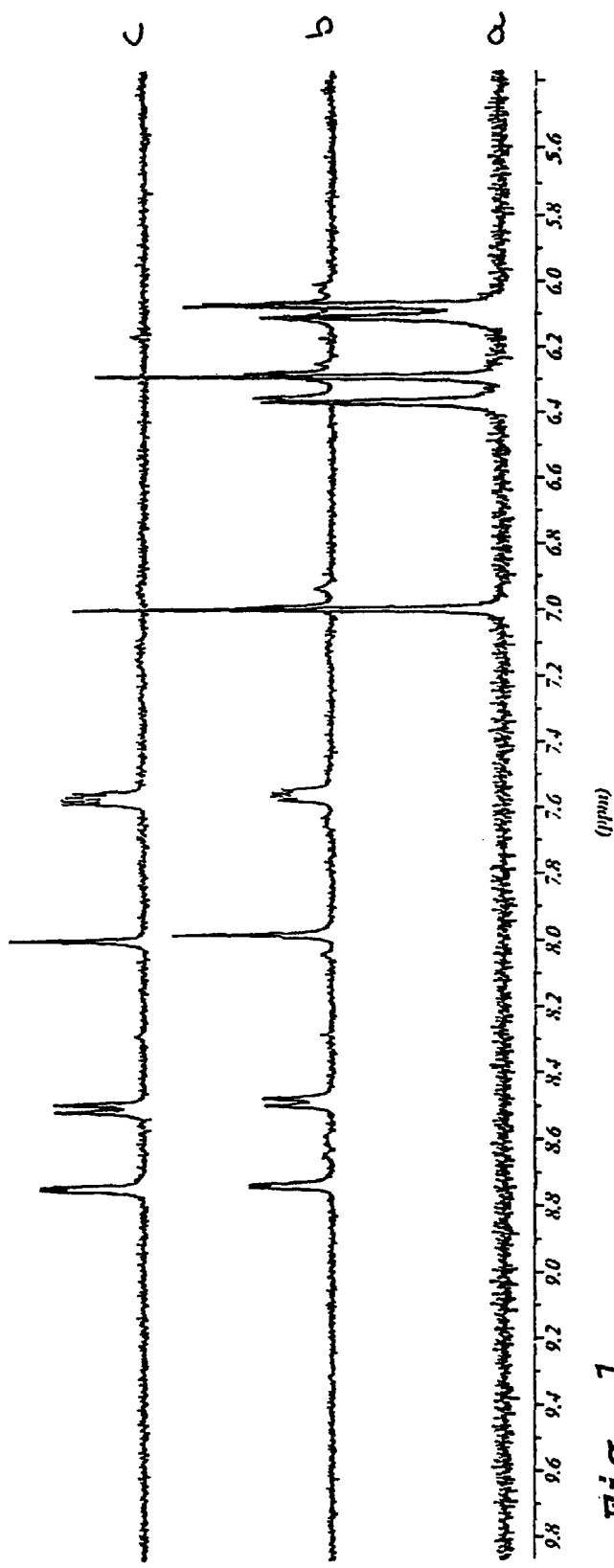
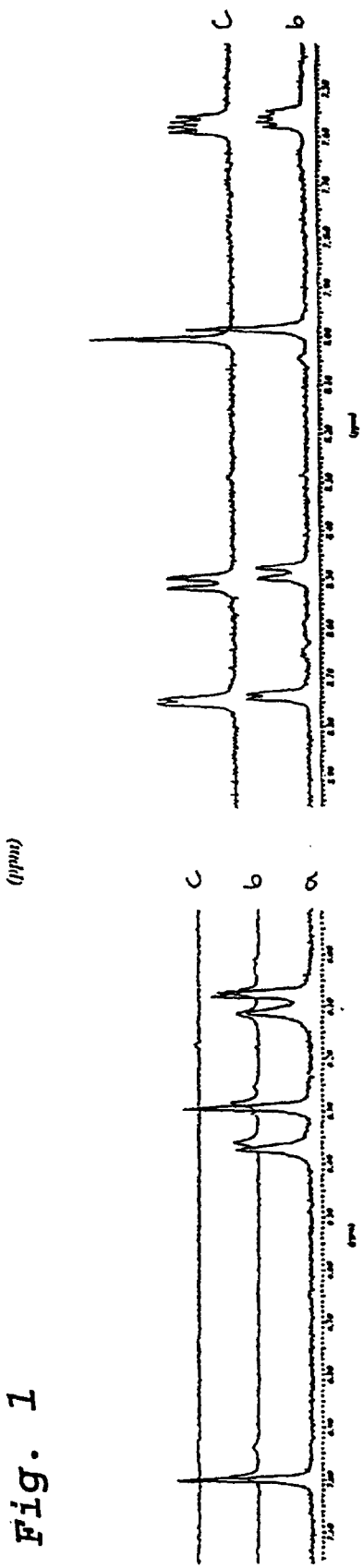
Fig. 1
Fig. 2
Fig. 3

CLIOQUINOL FOR THE TREATMENT OF ALZHEIMER'S DISEASE

This application is a section 371 continuation-in-part of copending International application No. PCT/IB97/00983 filed Aug. 8, 1997, which is incorporated by reference herein in its entirety.

1. INTRODUCTION

The present invention is directed to methods of treatment and prevention of Alzheimer's disease by administering the chelating agent clioquinol. The clioquinol may be administered in combination with vitamin $B_{12}$.

2. BACKGROUND OF THE INVENTION

2.1. ALZHEIMER'S DISEASE

Alzheimer's disease, which is the single major cause of dementia in adults in industrialized societies, is a degenerative brain disorder characterized clinically by a progressive loss of memory, confusion, dementia and ultimately death. Histopathologically, Alzheimer's disease is characterized by the presence in the neocortex, especially the hippocampus, of two brain lesions: the neurofibrillary tangles (NFTs) of paired helical filaments (PHF) in the neurons and the neuritic (senile) plaques in the extracellular space. The formation of senile plaques is related to the appearance of the symptoms and signs of the disease, including amnesia. After the formation of senile plaques, neurofibrillary tangles are produced in the neuronal bodies. The formation of neurofibrillary tangles is related to the worsening of amnesia and other symptoms of dementia.

There are several animal models of Alzheimer's disease. In one model, the insertion and overexpression in mice of a mutant form of the human amyloid precursor protein gene as a minigene under the regulation of the platelet-derived growth factor β receptor promoter element causes the appearance of a syntaptic pathology and amyloid-β peptide deposition in the brain of the mice. These changes in the brains of transgenic animals are similar to those seen in human Alzheimer's disease (Games et al., 1995, Nature 373:523–527).

In a similar model, transgenic mice were generated by using a promoter derived from the mouse neurofilament-light gene to drive expression in nerve cells of the mouse 42-amino acid Aβ protein (LaFerla et al., 1995, Nat. Genet. 9:41–47). Such mice also exhibit insoluble Aβ deposition in the brain.

A major component of the amyloid deposits in Alzheimer's disease is a polypeptide referred to herein as Aβ (Amyloid-beta). Aβ also accumulates in the wall and the lumen of the brain vessels. Aβ is normally a soluble component of the cerebrospinal fluid where it is found in concentrations of about 3–5 nM. Aβ may have 39 to 43 amino acids, typically 40 amino acids, in the mature form and is derived as a proteolytic cleavage product from a cell surface protein called the amyloid precursor protein (APP) (Kang et al., 1987, Nature 325:733–736). The normal function of Aβ is not known at present but might be to form cation selective channels across cell membranes (Kawahara et al., 1997, Biophysical Journal 73/1, 67–75).

The major form of Alzheimer's disease is sporadic and has a late onset, whereas a small percentage of cases are familial and have an early onset. Some of the familial cases of Alzheimer's disease are strongly associated with one or more mutations at different sites on the Aβ precursor protein, the gene of which lies on chromosome 21. Whether these mutations are the cause of Alzheimer's disease in the affected patients, however, has not been proven experimentally.

The plaques are not unique to Alzheimer's disease. The senile plaques are also seen in Down syndrome and in both aged human and animal brains. The numbers of plaques in non-demented aged humans are sometimes similar to those seen in Alzheimer's disease cases (Katzman et al., 1988, Ann. Neurol. 23:138–144).

The precipitation of synthetic Aβ has been shown to be caused by several environmental factors including low pH, high salt concentrations and the presence of metals, e.g., zinc, copper, and mercury (Bush et al., 1995, Science 268:1921–1923). It has been reported that Aβ itself specifically and saturably binds zinc with a high affinity binding ($K_D$=107 nM) at a molar ratio of 1:1 (zinc: Aβ) (Bush et al., 1994, J. Biol. Chem. 269:12152–12158). This binding takes place at physiological concentrations of zinc (Bush et al., 1994, Science 265:1464–1467).

There is a strong supposition that the removal of amyloid deposits from patients suffering from Alzheimer's disease will alleviate the symptoms of Alzheimer's disease. Therefore, several attempts have been made to prepare a drug for the removal of amyloid deposits, as methods for healing Alzheimer's disease are urgently sought.

International Publication No. WO 93/10459, dated May 27, 1993, discloses a method for the treatment of Alzheimer's disease by administering a zinc binding agent. As preferred compounds, phytic acid, desferri-oximine, sodium citrate, EDTA, 1,2-diethyl-3-hydroxy-pyridin-4-one, and 1-hydroxyethyl-3-hydroxy-2-methyl-pyridin-4-one are mentioned.

German publication DE 39 32 338, dated Apr. 11, 1991, discloses the use of an aluminum chelator, such as 8-hydroxy-quinoline, for the treatment of Alzheimer's disease.

U.S. Pat. No. 5,373,021, dated Dec. 13, 1994, discloses disulfiram and its salts and analogs. According to this patent, disclosed compounds may be used to reduce neurological damage caused by Alzheimer's disease.

The hitherto known compounds suggested for the treatment of Alzheimer's disease have several drawbacks, which has prevented their widespread use. Most of the compounds are unable to penetrate the blood-brain-barrier and thus cannot readily reach the areas in which the amyloid is deposited. Disulfiram, which may penetrate the blood-brain-barrier, has the drawback that when it is combined by a patient with ethyl alcohol, it causes severe adverse reactions, including headaches, nausea, vomiting, sweating, thirst, weakness, and low blood pressure.

The most extensively studied chelator is EDTA. However, the chelating effect of EDTA is relatively weak towards zinc and copper. Furthermore, EDTA cannot penetrate the blood-brain-barrier and is considered relatively toxic.

2.2. CLIOQUINOL

Clioquinol has been formulated and administered in various ways, at various doses (Ozawa et al., 1986, Acta Nueropathol (Berl) 69:272–277; Yamanaka et al., 1973, J. Biochem. 73:993–998; Sobue et al., 1971, Neurology 21:168–173; Tamura et al., 1973, Clinica Chimica Acta. 47:13–20; Jack and Riess, 1973, J. Pharm. Sci. 62(12):1929–1932; Baumgartner et al., 1979, Journal of Neurology, Neurosurgery, and Psychiatry 42:1073–1083, Kono, 1975, Japan. J. Med. Sci. Biol. 28:1–21; Sargeaunt and Lumsden, 1976, Transactions of the Royal Society of Tropical Medicine and Hygiene 70(l):54–56; Nakae et al., 1973, Lancet 171–173; Mumenthaler et al., 1979, Journal of Neurology, Neurosurgery, and Psychiatry 42:1084–1090; Schmid et al., 1973, Arzneim.-Forsch. (Drug Res.) 23(11):1560–1566; Oakley, 1973, JAMA 225(4):395–397; David et al., 1943, American J. Trop. Med., 24:29–33; Thomas et al.,1984, Journal of the Neurological Sciences 64:277–295; Yoshimura, 1992, Molecular and Chemical Neuropathology 16:59–84; Nakae, 1974, Japan Public Health Journal 15:607–611; Tateishi, 1973, Japan Public Health Journal 15:187–196; Degen et al., 1979, Dermatologica 159:295–301; Goto et al., 1982, J. Toxicological Sciences 7:1–12).

Clioquinol (5-chloro-7-iodo-8 hydroxyquinoline) was previously frequently used for the treatment of various disorders, such as amoebiasis and non-specific infectious diarrhea (Kono, 1975, Japan J. Med. Sci. Biol. 28:1–19, Meade, 1975, Brit. J. Prev. Soc. Med. 29:157–169). However, the use of clioquinol was stopped in Japan when the Japanese Government officially banned the sale in September 1970. The ban was motivated by the presumption that clioquinol caused subacute myelo-optico-neuropathy (SMON). Subsequently, clioquinol was withdrawn from the market in most other countries of the world on the recommendation of the World Health Organization.

SMON develops with an acute or subacute onset preceded by abdominal disorders and is characterized by dysesthesia of the legs, sensory disturbances, a variable degree of motor weakness, and visual loss. Corresponding to these clinical findings, SMON reveals pathologically symmetrical degeneration in peripheral nerves, spinal cord, posterior column, cardiac-spinal tract, and optic nerves.

The occurrence of SMON was confined to Japan even though clioquinol was prescribed worldwide and not only in Japan. In the published literature no systematic pathological features resulting from the administration of clioquinol have been described other than the cases of SMON in Japan.

Although, in March 1972, the SMON Research Commission in Japan established a guideline for the treatment of SMON, wherein vitamin $B_{12}$ was recommended to be administered as part of a supply of various vitamins (Jap. Med. Sci. Biol. 28 Suppl. (1975)), it was never recognized that the deficiency of vitamin $B_{12}$, at least to some extent, might be responsible for SMON. Actually, the effect of vitamin $B_{12}$ in the treatment of SMON has been contested by Okuda, K. ("On vitamin $B_{12}$ metabolism in SMON patients years after the onset." Report of SMON Research Commission in 1972 (1973) 86), who reported that the vitamin $B_{12}$ level in the serum of SMON patients is normal. It was also observed that there may be pathological differences between SMON and $B_{12}$ deficiency (Ricoy et al., 1982, J. Neurol. Sci. 53:241–251.) Hence, it was supposed that the administration of vitamin $B_{12}$ would not produce any improvement in the symptoms and signs of SMON.

After the withdrawal of clioquinol from the market there was a dramatic disappearance of new cases of SMON. At present, clioquinol is used topically due to its antibacterial and anti-fungal activity in skin infections.

Clioquinol has recently been shown to be effective in the treatment of Heliocobacter pylori (see International Publication No. WO 95/31199, dated Nov. 23, 1995) and neurotoxic injury (see International Publication No. WO 97/09976, dated Mar. 20, 1997 of Washington University).

The chelating ability of clioquinol is known for Fe, Co, Ni and Zn (Kidani et al., 1974, Jap. Analyst 23:1375–1378).

Using mass spectrophotometry the coordination number for clioquinol for Co(II), Ni(II), Cu(II) and Zn(II) is 2, whereas the coordination number for Fe(III) is 3. Reportedly, injected preparations of clioquinol have crossed the blood-brain-barrier, leaving concentrations thereof in the brain on the order of 20 $\mu l/ml$ when administered at dosages of 10–20 mg/kg (Tateishi et al., 1973, Psychiat.

Neurol. Jap. 75:187–196 and Tamura, 1975, Tap. J. Med. Sci. Biol. Suppl 28:69–77). The concentration of clioquinol was also found to be high in such areas of the brain as the hippocampus.

Using microautoradiographic techniques, clioquinol has been shown in monkeys to form zinc chelates in the hippocampus. The Zn(II) chelates were mainly found in the terminal axodendritic boutons of the mossy fibres. Unconjugated clioquinol has an extremely rapid penetration into the nervous system when injected intravenously, with the ability to cross the blood-brain-barrier (Shiraki, 1979, In: Intoxications of the Nervous System. Part II. Handbook of Clinical Neurology, Vinken et al. eds., North Holland Publishing Co., NY, pp. 115–139).

Citation or discussion of a reference hereinabove shall not be construed as an admission that such is prior art to the present invention.

3. SUMMARY OF THE INVENTION

The present invention provides methods of treating or preventing Alzheimer's disease by administering clioquinol alone or in combination with vitamin $B_{12}$.

Also according to the present invention, a pharmaceutical composition is provided, which comprises clioquinol, vitamin $B_{12}$, and, optionally, pharmaceutically acceptable carriers.

4. BRIEF DESCRIPTION OF THE FIGURES

FIG. 1 depicts the NMR spectra of three solutions. Solution a contained vitamin $B_{12}$ (hydroxycobalamin), at a concentration of 2.6 mM. Solution b contained a mixture of 2.6 mM vitamin $B_{12}$ and 10 mM clioquinol glucuronide (mole ratio of about 1:4). Solution c contained 10 mM clioquinol glucuronide.

FIG. 2 depicts the right half of FIG. 1 expanded for easier comparison of the resonance positions.

FIG. 3 depicts the left half of FIG. 1 expanded for easier comparison of the resonance positions.

5. DETAILED DESCRIPTION OF THE INVENTION

Figure 4:
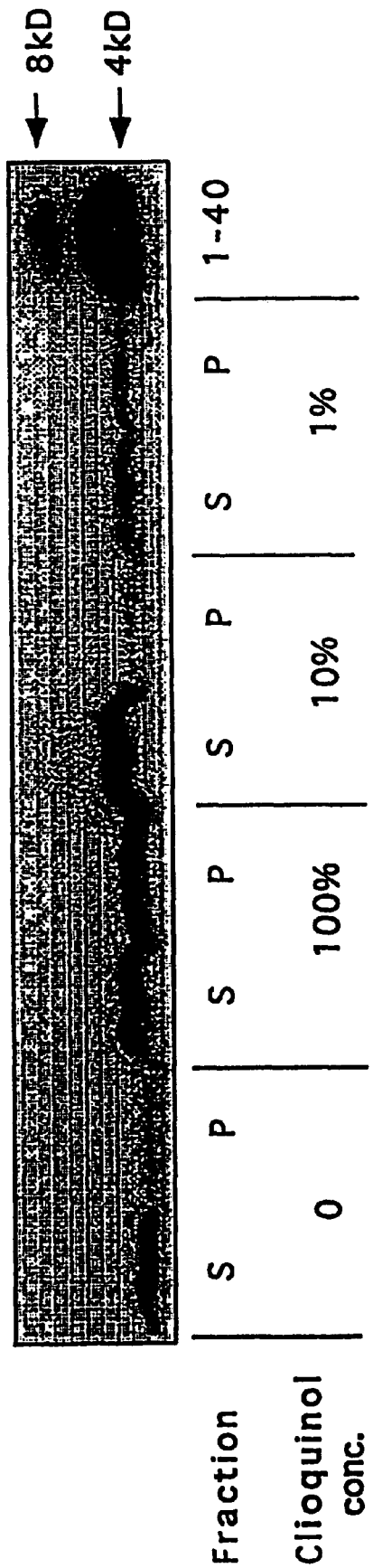
FIG. 4 depicts the amounts of β amyloid found in the supernatants of brain specimen homogenates taken from patients diagnosed with Alzheimer's disease after the homogenates were exposed to several concentrations of clioquinol (100%=800 nM clioquinol). The lane labeled "1–40" contains TCA precipitated synthetic Aβ.

In the following the invention will be explained in further detail.

The present invention provides methods of treating or preventing Alzheimer's disease by administering clioquinol or a combination of clioquinol and vitamin $B_{12}$.

The relationship between SMON and clioquinol has been investigated and an explanation of the development of SMON as a consequence of clioquinol administration has been discovered. Thus, a further object of the present invention is to remove or alleviate or prevent at least some of the side effects that occur when clioquinol is administered.

This object is achieved through the co-administration of vitamin $B_{12}$ with clioquinol.

In the following the invention will be explained in further detail. The proposed mechanism of action of the invention is not intended to limit the invention to said mechanism.

It is known that clioquinol is excreted through the kidneys as glucuronide or sulfate derivatives (Kotaki et al.: "Enterohepatic circulation of clioquinol in the rat", J. Pharmacobiodyn. 1984 June; 7(6):420–5 and Jurima et al.: "Metabolism of 14C-iodochlorhydroxy-quinoline in the dog and the rat", J. Pharmacobiodyn. 1984 March; 7(3): 164–70), e.g., as the compound methyl (5-chloro-7-iodo-quinolyl-2',3',4'-tri-o-acetyl-glucopyranosid)uronate. For short, this compound is referred to as clioquinol glucuronide in the following.

The detoxification of hydrophobic substances, such as clioquinol, in the body predominantly occurs in the liver. Therefore, it is believed that the clearance of clioquinol happens as follows: Clioquinol is converted to clioquinol glucuronide in the liver. Following the formation, the water soluble clioquinol glucuronide is secreted to the bile. The bile enters the intestine, wherein a major amount of the clioquinol glucuronide is evacuated in the stool. A certain amount of the clioquinol glucuronide is resorbed from the intestine to the blood. The clioquinol glucuronide is filtered from the blood in the kidneys and appears in the terminal urine.

By treating mice with clioquinol and subsequently administering a radioisotope of vitamin $B_{12}$ ($[^{57}Co]$-cyanocobalamine), it is shown in Example 1 below that the concentration of vitamin $B_{12}$ in the brain and the liver of the clioquinol-treated mice remains at a normal level, whereas the concentration of the radioisotope of vitamin $B_{12}$ is decreased in the kidney of such mice compared to the normal level. This finding suggests a metabolism of vitamin $B_{12}$ being dependent on clioquinol. Further, the finding suggests that the kidneys are the target organs, wherein the clioquinol dependent metabolism occurs.

In order to investigate a possible interaction between clioquinol glucuronide and vitamin $B_{12}$, an experiment was designed, wherein clioquinol glucuronide and vitamin $B_{12}$ were mixed in water. The mixture was analyzed by $^1H$ NMR. The $^1H$ NMR spectra, see FIGS. 1–3, show that some of the resonances of vitamin $B_{12}$ (corresponding to the benzimidazole moiety) have shifted, and the same is observed for two resonances of the clioquinol glucuronide (corresponding to the quinoline moiety). It is believed by applicant that similar results would be expected using free clioquinol, however clioquinol cannot be dissolved in aqueous solutions for NMR testing.

The results indicate a hydrophobic interaction between clioquinol glucuronide and vitamin $B_{12}$, possibly between the benzimidazole moiety of the vitamin $B_{12}$ and the quinoline moiety of clioquinol glucuronide.

Vitamin $B_{12}$ is normally resorbed actively from the renal plasma after it has been filtered. In that way the body recovers most of the vitamin $B_{12}$ that would otherwise have been lost in the urine. It has recently been demonstrated that the resorption of vitamin $B_{12}$ is mediated by the action of the membrane protein megalin (Moestrup et al. Proc. Natl. Acad. Sci. 1996; 93(16):8612–7). The megalin is shown to have a strong affinity towards the binding of a complex formed by vitamin $B_{12}$ and the transport protein transcobalamin.

Based on the new finding reported herein, viz. that vitamin $B_{12}$ binds to clioquinol glucuronide, it is believed that vitamin $B_{12}$ does not bind to the megalin protein and/or the transcobalamin when it is already bound to the clioquinol glucuronide. Thus, the resorption of vitamin $B_{12}$ will fail and the body will suffer from vitamin $B_{12}$ deficiency after a certain time period of clioquinol administration if the body is not supplied with enough new vitamin $B_{12}$ through the normal diet.

Since the only source of vitamin $B_{12}$ is microorganisms, only microorganisms and species eating microorganisms contain vitamin $B_{12}$. Thus, diets low in meat and/or microorganisms will evidently cause vitamin $B_{12}$ deficiency. If persons are supplied with diets with a too low content of vitamin $B_{12}$, the administration of clioquinol will worsen the condition as the resorption of $B_{12}$ is prevented by the competitive binding of clioquinol with megalin. The fact that the Japanese diet in the 1960s predominantly consisted of vegetables and cereals, especially rice (Kromhout D., et al.: "Food consumption pattern in the 1960s in seven countries", Am. J. Clin. Nutri. 49:889–894, 1989), may explain why the SMON disease was confined to Japan.

At present, it is believed that clioquinol and $A\beta$ competitively chelate zinc and other heavy metals. Clioquinol is regarded as the stronger chelator and will, therefore, predominately capture the heavy metal ions. Thus, $A\beta$ from precipitated zinc-$A\beta$ will be resolubilized into the surrounding fluid because clioquinol will capture the zinc ions. The complex of clioquinol and zinc will penetrate the blood-brain-barrier and be cleared from the organism.

Since clioquinol is a relatively strong chelator, it may also chelate metal ions from enzymes or prosthetic groups. Therefore, it might be desirable to supplement trace metal ions or prosthetic groups to clioquinol treated patients, especially when establishing prolonged clioquinol treatments. Vitamin $B_{12}$ contains cobalt.

The present invention solves the problem of clioquinol induced vitamin $B_{12}$ deficiency and the subsequent development of SMON by the co-administration of vitamin $B_{12}$ and clioquinol. Compositions, formulations, and kits for such co-administration are provided.

5.1. TREATMENT OF ALZHEIMER'S DISEASE

The invention provides a method of treating or preventing Alzheimer's disease (AD) with clioquinol or with the combination of clioquinol and vitamin $B_{12}$. Clioquinol is believed to have the ability to penetrate the blood-brain barrier, to effectively chelate heavy metals to prevent the aggregation of amyloid, and to redissolve amyloid deposit.

It could not have been predicted that clioquinol had the ability to redissolve zinc precipitated $A\beta$.

The following proposed mechanism of action of the invention is not intended to limit the invention to said mechanism. At present, applicant believes that clioquinol and $A\beta$ competitively chelate zinc and other heavy metals. Clioquinol is regarded as the stronger chelator and will, therefore, predominately capture the heavy metal ions. Thus, zinc bound to $A\beta$ in $A\beta$ aggregates will be bound by clioquinol. The removal of zinc by clioquinol will resolubilize the $A\beta$ protein. The complex of clioquinol and zinc should penetrate the blood-brain-barrier and be cleared from the organism.

Clioquinol may be administered in any appropriate amount in any suitable galenic formulation and following any regime of administration.

Preferably, the amount of daily administration will be from 10 mg to 750 mg clioquinol depending on the condition of the patient. A typically daily dosage is 100 mg. Alternatively, from 10 mg to 250 mg, preferably 100 mg clioquinol, three times daily, may be administered. A daily dosage of up to 750 mg for a period of two weeks is considered to present no risk of neurotoxicity or other side effects. In another embodiment, the daily dose of clioquinol is less that 100 mg.

For methods which include the administration of vitamin $B_{12}$, a typical daily dose of vitamin $B_{12}$ is, for example, 5 μg to 2 mg, preferably 0.5 to 1 mg. The actual administered amounts of clioquinol and vitamin $B_{12}$ may be determined by a supervising physician.

For the prevention of the onset of the symptoms and signs of Alzheimer's disease, or for the delay of the symptoms and signs in the evolution of the disease, daily clioquinol dosages of 100 mg or less can be administered for long periods, viz. up to ten years.

By way of example, but not limitation, methods of the invention can be used for: 1) patients diagnosed with AD at any clinical stage of the disease, 2) the prevention of AD in patients with early or prodromal symptoms or signs, and 3) the delay of the onset or evolution or aggravation of the symptoms and signs of AD. The methods of the invention will be, for example, useful for the treatment of AD, the improvement or alleviation of any symptoms and signs of AD, the improvement of any pathological or laboratory findings of AD, the delay of the evolution of AD, the delay of onset of any AD symptoms and signs, the prevention of occurrence of AD, and the prevention of the onset of any of the symptoms and signs of AD.

The actual administered amount is to be decided by the supervising physician and may depend on multiple factors, such as, the age, condition, file history, etc., of the patient in question.

The dose of clioquinol optimal in vivo for the resolubilisation of Aβ can be determined by a physician upon conducting routine experiments. An example of such an experiment is the monitoring of soluble Aβ in the cerebrospinal fluid (CSF) (WO 93/10459, dated May 27, 1993 of University of Melbourne). Beginning with relatively low doses (10–25 mg/day), a physician can monitor the amount of solubilized Aβ in a patient's CSF. If there is no increase in solubilized Aβ in response to the clioquinol administration, indicative of resolubilization of zinc-Aβ aggregates, the dosage can be raised until such an increase is observed.

If clioquinol is going to be administered for a prolonged period, it is preferably administered intermittently. In a first period clioquinol may be administered, e.g., for one to three weeks followed by a wash-out period, which may provide for the lessening of any unwanted side effects of clioquinol. The duration of the wash-out period may be one to four weeks. After the wash-out period the first period may be repeated. If vitamin $B_{12}$ is to be administered, such administration may take place during the clioqinol administration period, during the wash-out period, or during both periods. The long-term intermittent therapy will provide not only for the resolubilisation of zinc-Aβ aggregates, but also for the prophylactic inhibition of the formation of zinc-As aggregates.

The intermittent administration of clioquinol will also reduce the toxicity potential of the drug, which means that the treatment may be extended throughout the evolution of the disease.

Prior to administration to humans, the efficacy is preferably shown in animal models. Any animal model for Alzheimer's disease known in the art can be used.

The subject, or patient, to be treated using the methods of the invention is an animal, e.g., a mammal, and is preferably human, and can be a fetus, child, or adult.

5.2. PHARMACEUTICAL COMPOSITIONS

The pharmaceutical compositions according to the present invention preferably comprise one or more pharmaceutically acceptable carriers and the active constituents. The carrier(s) must be "acceptable" in the sense of being compatible with the other ingredients of the composition and not deleterious to the recipient thereof. In a preferred embodiment, the clioquinol and/or vitamin $B_{12}$ in the pharmaceutical composition is purified.

It will be appreciated that the amounts of clioquinol and vitamin $B_{12}$ required for said treatment or prevention will vary according to the route of administration, the disorder to be treated, the condition, age, and file history of the subject, the galenic formulation of the pharmaceutical composition, etc.

Preferably, the clioquinol used in the invention is of high purity, such as that provided by Spectrum Quality Products, specification: USP 23; however any suitable preparation of clioquinol can be used in the methods and compositions of the invention.

Preferably, the vitamin $B_{12}$ used in the invention is of high purity, such as that provided by Hoffman La Roche, Ltd., specification: pharmaceutical grade; however any suitable preparation of vitamin $B_{12}$ can be used in the methods and compositions of the invention.

In general, a suitable (therapeutically effective) amount of clioquinol in the pharmaceutical composition is, for example, 5 to 250 mg, preferably 10 to 50 mg. A suitable amount of vitamin $B_{12}$, effective to inhibit clioquinol related side effects, in the pharmaceutical composition is, for example, 5 μg to 2 mg, preferably 0.5 to 1 mg. The actually administered amounts of clioquinol and vitamin $B_{12}$ may be decided by a supervising physician. Clioquinol and vitamin $B_{12}$ can be in the same composition for administering in combination concurrently, or in different compositions for administering concurrently but separately, or sequentially.

Therapeutic formulations include those suitable for parenteral (including intramuscular and intravenous), oral rectal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing clioquinol and vitamin $B_{12}$, and compressing this mixture in a suitable apparatus into tablets having a suitable size. Prior to the mixing, the clioquinol may be mixed with a binder, a lubricant, an inert diluent and/or a disintegrating agent and the vitamin $B_{12}$ may be mixed with a diluent, a lubricant and/or a surfactant. Alternatively, the vitamin $B_{12}$ may be omitted.

In a preferred embodiment, free-flowing clioquinol powder is mixed with a binder, such as microcrystalline cellulose, and a surfactant, such as sodium lauryl sulphate until a homogeneous mixture is obtained. Subsequently, another binder, such as polyvidone, is transferred to the mixture under stirring. When a uniform distribution is obtained an aqueous solution of vitamin $B_{12}$ is added under constant stirring. This mixture is passed through granulating sieves and dried by desiccation before compression into tablets in a standard compressing apparatus.

In a second preferred embodiment, free-flowing clioquinol powder is mixed with surfactants and/or emulsifying agents, such as Sapamine® (N4'-stearoyl amino phenyl)-trimethylammonium methyl sulfuric acid) and lactose monohydrate until a uniform distribution of the constituents is obtained. A second preparation containing a disintegrating agent, such as maize starch, is added to the clioquinol mixture under continuous stirring. Such a second preparation may be prepared by adding excess boiling water to a maize starch suspended in cold water. An aqueous solution of vitamin $B_{12}$ is added to the clioquinol mixture. The final mixture is granulated and dried as above and mixed with maize starch and magnesium stearate and finally compressed into tablets in a standard apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising clioquinol and vitamin $B_{12}$ that is to be reconstituted by dissolving in a pharmaceutically acceptable carrier that dissolves vitamin $B_{12}$ and clioquinol, e.g., an aqueous solution of carboxymethylcellulose and lauryl sulfate.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J. Macromol. Sci. Rev. Macromol.

Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In one embodiment of the pharmaceutical composition according to the invention, the active constituents, i.e., vitamin $B_{12}$ and clioquinol, are comprised as separate entities. The two entities comprising vitamin $B_{12}$ and clioquinol, respectively, may be administered simultaneously or sequentially. For example, clioquinol can be administered, followed by vitamin $B_{12}$ administered within a day, week, or month of clioquinol administration. If the two entities are administered sequentially, the entity comprising clioquinol is preferably administered for one to three weeks followed by a wash out period of one to four weeks during which the entity comprising vitamin $B_{12}$ is administered, but not the entity comprising clioquinol. After the wash out period, the treatment can be repeated.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLES

Example 1

The influence of clioquinol on vitamin $B_{12}$ in vivo was studied.

Six week old male mice were divided into two groups, a control group and a group which was injected with clioquinol(50 mg/kg/day). After three days, all of the mice were injected with [$^{57}$Co]-cyanocobalamine. After two days, the animals were sacrificed, and the brain, liver and kidney were dissected and counted in a gamma-counter as thousand cpm/g tissue (wet weight)±SEM. The radioactivities in each of the groups are stated in Table 1 below:

TABLE 1

| Treatment | Brain | Liver | Kidney |
| --- | --- | --- | --- |
| Control | 9.4 ± 0.9 | 97 ± 8 | 895 ± 207 |
| Clioquinol | 8.4 ± 1.5 | 85 ± 21 | 252 ± 61 |

A comparison of the results show that there were no significant changes in the amount of radioactivity accumulation in the brain and the liver. A reduction in the amount of vitamin $B_{12}$ trapped in the kidneys was apparent. This result suggests that clioquinol interferes with the vitamin $B_{12}$ metabolism in the kidneys but not elsewhere in the body.

Example 2

In this example, a metabolite of clioquinol was synthesized. It is known that the clioquinol is excreted through the kidneys as glucuronide derivatives of clioquinol (Kotaki H., et al.: "Enterohepatic circulation of clioquinol in the rat", J. Pharmacobiodyn. 1984 June; 7(6):420–5 and Jurima et al.: "Metabolism of 14C-iodochlorhydroxy-quinoline in the dog and the rat", J. Pharmacobiodyn. 1984 March; 7(3):164–70). The transformation of clioquinol to the corresponding glucuronide presumably takes place in the liver. Following the formation of clioquinol glucuronide in the liver, it is eventually transferred to the kidneys for excretion in the urine.

A glucuronide derivative of clioquinol in the form of methyl(5-chloro-7-iodo-quinolyl-2',3',4'-tri-O-acetyl-glycopyranosid)uronate was prepared according to the following reaction scheme:

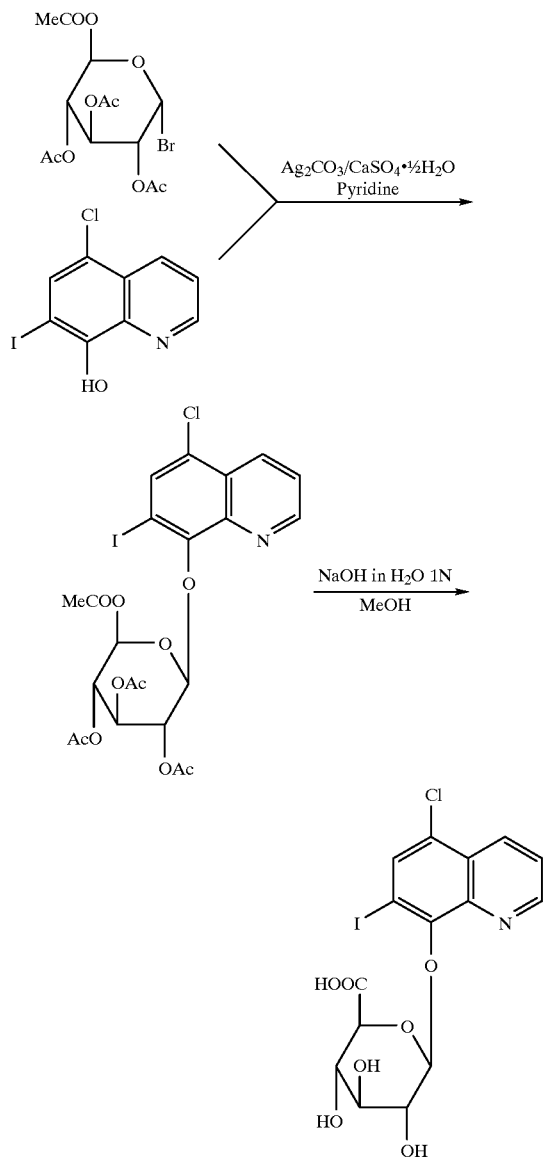

A mixture of 5-chloro-8-hydroxy-7-iodo-quinoline (50 mg, 0.164 mmol), methyl 1-bromo-1-deoxy-2,3,4-tri-O-acetyl-D-glucopyranosiduronate (65 mg, 0.164 mmol), CaSO$_4$.H$_2$O (35 mg) and pyridine (1.5 ml) was stirred at room temperature for min. Freshly prepared Ag$_2$CO$_3$ (35 mg) was added to the reaction mixture and the suspended solution was stirred at room temperature for 20 hours in the dark. Subsequently, the reaction product was deacetylated by 1 N aqueous NaOH.

The reaction mixture was diluted with CH$_2$Cl$_2$ (10 ml), filtered and the solvent evaporated under reduced pressure. The above product was purified by flash chromatography (TLC: CH$_2$Cl$_2$/MeOH 99/1, eluent: CH$_2$Cl$_2$/.MeOH 99.5/0.5).

NMR (400 MHz, CDCl$_3$) 2.04 (s, 3H, Ac), 2.09 (s, 3H, Ac), 2.13 (s, 3H, Ac), 3.68 (s, 3H, Me), 3.99 (d, 1H, 5' H), 5.40–5.52 (m, 3H, 2', -3', -4'-H), 6.29 (d, 1H, 1' -H), 7.56 (m, 1H, 3H), 7.99 (s, 1H, 6-H), 8.52 (d, 1H, 4-H), 8.93 (s, 1H, 2-H).

This compound is referred to as clioquinol glucuronide in the following.

Example 3

The interaction of vitamin B$_{12}$ with clioquinol glucuronide as prepared in example 2, was studied using nuclear magnetic resonance (NMR) spectroscopy.

As the clioquinol glucuronide is soluble in water, the study was undertaken in buffered water at PH=6.5. Three different solutions were prepared and their $^1$H NMR spectra were recorded in a DRX 400 MHz spectrophotometer at 20° C. Solution a) contained free vitamin B$_{12}$ (hydroxycobalamin) in a concentration of 2.6 mM. Solution b) contained a mixture of 2.6 mM vitamin B$_{12}$ and 10 mM clioquinol glucuronide (mole ratio of about 1:4). Solution c) contained 10 mM clioquinol glucuronide.

In FIG. 1 the spectra of the three solutions are presented for the aromatic region (5.5–9.8 ppm). The differences are quite small but obvious in the expansion shown of FIG. 2 and FIG. 3, respectively. Some of the resonances of vitamin B$_{12}$ (corresponding to the benzimidazole moiety) have shifted (see FIG. 2), and the same is observed for two resonances of the clioquinol glucuronide (corresponding to the quinoline moiety) (see FIG. 3).

The results suggest an interaction between clioquinol glucuronide and vitamin B$_{12}$, possibly of a hydrophobic nature between the benzimidazolemoiety of the vitamin B$_{12}$ and the quinoline moiety of clioquinol glucuronide.

The hydrophobic binding of vitamin B$_{12}$ to clioquinol glucuronide is believed to cause the vitamin B$_{12}$ to be excreted from the body together with clioquinol glucuronide, thus preventing resorption of vitamin B$_{12}$, which would eventually lead to a vitamin B$_{12}$ deficiency. Therefore, vitamin B$_{12}$ deficiency is believed to be, at least to some extent, the underlying cause of SMON.

Example 4

Preparation of a pharmaceutical composition comprising clioquinol and vitamin B$_{12}$. 250 g of clioquinol (5-chloro-7-8-quinoline) was mixed for a period 3 minutes with 1657.5 g micro crystalline cellulose and 20 g sodium lauryl sulphate. An aqueous solution of 25 g polyvidone and an aqueous solution of 5.0 g vitamin B$_{12}$ (cyanocobalamine) was added to the clioquinol containing powder mixture under stirring. This mixture was passed through granulating sieves (2.5 mm) and desiccated for a period of 20 hours at 40° C. The dry mixture (sieved at 1.25 mm) was blended with 30 g sodium lauryl sulphate and 12.5 g magnesium stearate. This mixture was formed into tablets having a diameter of 8.0 mm and a weight of 200 mg.

Example 5

Preparation of a pharmaceutical composition comprising clioquinol and vitamin B$_{12}$. 250 g of clioquinol (5-chloro-7-iodo-8-quinoline) was mixed with 200 g sapamine® (N-

(4'-stearoylamino-phenyl)-trimethylammonium methyl sulfuric acid) and 1025 g lactose mono hydrate for a period of 5 minutes. 300 g of boiling water was added to a mixture of 100 g maize starch in 100 g cold water. The maize suspension, cooled to 40° C. was added to the clioquinol containing powder mixture under continuous stirring. Subsequently, an aqueous solution of 5 g vitamin $B_{12}$ was added. The mixture was granulated using a 2.5 mm sieve and desiccated for 18 hours at 40° C. The dry granules were mixed with 400 g maize starch and 20 g magnesium stearate. The final mixture was formulated into tablets having a diameter of 8.0 mm and a weight of 200 mg.

Example 6

The resolubilization of amyloid aggregates by clioquinol was studied. 5.3 g of clioquinol was suspended ith agitation in 200 ml of n-decane. The undissolved aterial was allowed to settle. Weighing the dried undissolved clioquinol after blowing off the decane indicated that only 2% of the clioquinol dissolved in the decane. 100 ml of the (light yellow) supernatant was agitated together with 100 ml of PBS pH 7.4 and the phases allowed to separate. The PBS (lower phase) was collected and filtered to remove the residue which formed at the phase interface upon extraction with the organic solvent. Assuming that 2% of the clioquinol dissolved in the n-decane, and assuming that the partitioning coefficient is 1/1750 with PBS at 1:1 mixtures of decane/clioquinol, the concentration of clioquinol in the PBS is 800 nM.

Brain specimens were obtained for which a histopathological diagnosis of Alzheimer's disease was confirmed. Duplicate 0.5 g specimens of frontal lobe neocortex were homogenized in 3 ml of the clioquinol/PBS solution at 100%, 10% and 1% of the final PBS/clioquinol extract and PBS alone.

The homogenates were centrifuged at 150,000 xg for thirty minutes and the supernatants collected and held on ice (fraction "S"). The pellets were subjected to an identical homogenization and centrifugation regime and the resulting supernatants again collected (fraction "P")

1 ml of each supernatant was treated with 200 $\mu$l of ice cold 10% TCA to precipitate total protein including A$\beta$. The resulting pellet was washed once with 100% ethanol and resuspended in 100 $\mu$l of TBS (tris 20 mM, NaCl 150 mM, pH 7.4).

7.5 $\mu$l of sample (S or P) was boiled for 5 min. with an equal volume of tris-tricine sample buffer containing 4% SDS and loaded onto a Novex pre-cast 10-20% tris-tricine gel followed by Western transfer onto nitrocellulose. Signal for A$\beta$ was detected using mAb W02 (raised against residues 5–16 of A$\beta$) and visualized using ECL. The sensitivity of the detection system is 5–10 pg.

To validate the TCA precipitation for A$\beta$ 1 $\mu$g of synthetic A$\beta$ 1–40 was added to 1 ml of PBS containing 10% BSA and the solution was treated as above. Signal for A$\beta$ was etected in the precipitated pellet but not in the supernatant.

The result is indicated in FIG. 4.

As can be deduced from FIG. 4, the clioquinol was effective in promoting the solubilization of A$\beta$ in the concentrations tested. Furthermore, the optimal concentration was found to be "10%", indicating that one of the aggregation forms of A$\beta$, presumably the dimer, is more soluble in PBS than others.

While data are shown only for one specimen in FIG. 1, data for 19 other specimens all indicate the same tendency, viz. that clioquinol is effective in promoting the solubilization of A$\beta$.

Example 7

A comparison of the chelating abilities of EDTA and clioquinol was made. Samples of 10 ng synthetic A$\beta$ were placed in microtitre wells and caused to aggregate by the addition of 25 $\mu$M ZnCl. The aggregates were then transferred to a 0.2 $\mu$m nylon membrane by filtration. The aggregates were washed with 200 $\mu$l TBS alone, TBS containing 2 $\mu$M EDTA, and TBS containing 2 $\mu$M clioquinol. The membrane was fixed, probed with the anti A$\beta$ monoclonal antibody 6E10 and developed for exposure to ECL-film. The transmittance of the ECL-film was measured and the relative signal strength calculated based on 100% for TBS alone. The relative signal strength was 66% for EDTA and 49% for clioquinol.

The results indicate that clioquinol is a better chelator for zinc precipitated A$\beta$ than EDTA.

Example 8

The ability of clioquinol to resolubilize zinc-aggregated A$\beta$ was assessed. A 2.5 AM solution of A$\beta$ in TBS at a pH of 7.4 was prepared. 95% of the A$\beta$ was maintained in a soluble state. Addition of 30 $\mu$M zinc resulted in precipitation of the soluble A$\beta$ and only 43% was maintained in solution. The subsequent addition of 120 $\beta$M clioquinol to the zinc precipitated A$\beta$ resulted in an increase of soluble A$\beta$ to 70%.

The results indicate that clioquinol is able to redissolve zinc precipitated A$\beta$.

Example 9

A patient suffering from Alzheimer's disease is treated with the tablet described in Example 5 as follows:

In the first period of treatment, one tablet a day for two weeks is administered, followed by a two week wash-out period, during which vitamin $B_{12}$ administration alone is continued. The tablet containing vitamin $B_{12}$ alone is formulated identically to the tablet described in Example 5, except that clioquinol is omitted. After the wash-out period, the first period is repeated. During the treatment, the amount of solubilized A$\beta$ in the patient's cerebrospinal fluid (CSF) is monitored. If there is no increase in solubilized A$\beta$ in response to the clioquinol administration, indicative of resolubilization of zinc-A$\beta$ aggregates, the dosage is raised to two tablets once a day. An observed increase of solubilized A$\beta$ in the patient's CSF indicates that the treatment is effective at resolubilizing A$\beta$. Preferably, two more cycles of clioquinol in combination with vitamin $B_{12}$ followed by vitamin $B_{12}$ alone are administered.

Various publications are cited herein, the disclosures of which are incorporated by reference in their entireties.

The invention being thus described, it will be obvious that the same may be varied in many ways. Such variation are not to be regarded as a departure from the spirit and scope of the invention, and all such modifications, as would be obvious to a person skilled in the art, are intended to be included in the scope of the following claims.

What is claimed is:

1. A method of treating a subject having or suspected of having Alzheimer's disease comprising administering to the subject an amount of clioquinol effective to treat or prevent Alzheimer's disease.

2. The method according to claim 1 wherein the clioquinol is (a) administered for one to three weeks, followed by (b) a period of one to four weeks during which clioquinol is not administered.

3. A method of treating a subject having or suspected of having Alzheimer's disease comprising administering to the subject an amount of clioquinol effective to increase the solubility of amyloid-beta in the cerebrospinal fluid of said subject.

4. A method of treating a subject having or suspected of having Alzheimer's disease comprising administering to the subject (a) an amount of clioquinol effective to treat or prevent Alzheimer's disease, and (b) an amount of vitamin $B_{12}$.

5. The method according to claim 4 wherein the amount of vitamin $B_{12}$ is effective to inhibit a detrimental side effect of clioquinol administration.

6. The method according to claim 4 wherein a pharmaceutical composition comprising clioquinol is administered for one to three weeks, followed by a period of one to four weeks during which a pharmaceutical composition comprising vitamin $B_{12}$ is administered and clioquinol is not administered.

7. The method according to claim 4 wherein the clioquinol and vitamin $B_{12}$ are comprised in a single pharmaceutical composition.

8. The method according to claim 4 wherein the lioquinol and vitamin $B_{12}$ are administered sequentially.

9. The method according to claim 4 wherein the clioquinol and vitamin $B_{12}$ are administered substantially simultaneously.

10. The method according to claim 5 wherein a pharmaceutical composition comprising clioquinol is administered for one to three weeks, followed by a period of one to four weeks during which a pharmaceutical composition comprising vitamin $B_{12}$ is administered and clioquinol is not administered.

11. The method according to any one of claims 1 to wherein the subject is human.

12. The method according to claim 1 or 4, wherein the clioquinol is administered in an amount of 10 to 250 mg one to three times daily.

13. The method according to claim 1, wherein trace metals and/or prosthetic groups are administered together with or subsequent to the administration of clioquinol.

14. The method according to claim 1 or 4, wherein the clioquinol is administered intermittently.

15. The method according to claim 2, wherein trace metals and/or prosthetic groups are administered during the period of one to four weeks during which clioquinol is not administered.

16. The method according to claim 1, wherein the clioquinol is administered for up to ten years.

17. The method according to claim 1 or 4, wherein the clioquinol is formulated for oral administration.

18. The method according to claim 1 or 4, wherein the clioquinol is formulated for parenteral administration.

19. The method according to claim 1 or 4, wherein the clioquinol is formulated for intradermal administration.

20. The method according to claim 1 or 4, wherein the clioquinol is formulated in a capsule.

21. The method according to claim 1 or 3, wherein the clioquinol is purified.

22. The method according to claim 4, 5, 6 or 7 wherein the clioquinol and vitamin $B_{12}$ are each purified.

23. A pharmaceutical composition comprising an amount of clioquinol effective to treat or prevent Alzheimer's disease, and vitamin $B_{12}$.

24. The pharmaceutical composition according to claim 23, which further comprises a pharmaceutically acceptable carrier.

25. The pharmaceutical composition according to claim 23, wherein the amount of clioquinol is 5 to 250 mg.

26. The pharmaceutical composition according to claim 23, wherein the amount of clioquinol is 10 to 50 mg.

27. The pharmaceutical composition according to claim 23, wherein the amount of vitamin $B_{12}$ is 5 $\mu$g to 2 mg.

28. The pharmaceutical composition according to claim 25, wherein the amount of vitamin $B_{12}$ is 5 $\mu$g to 2 mg.

29. The pharmaceutical composition according to claim 23, wherein the amount of vitamin $B_{12}$ is 0.5 mg to 1 mg.

30. The pharmaceutical composition according to claim 23, wherein the composition is formulated for parenteral or intradermal administration.

31. The pharmaceutical composition according to claim 23, wherein the composition is formulated for oral administration.

32. The pharmaceutical composition according to claim 23, 24 or 25, wherein the pharmaceutical composition is formulated as a pill.

33. The pharmaceutical composition according to claim 23, 24 or 25, wherein the pharmaceutical composition is formulated as a tablet.

34. The pharmaceutical composition according to claim 23, 24 or 25, wherein the pharmaceutical composition is formulated as a capsule.

35. The pharmaceutical composition according to claim 23, 24 or 25, wherein the pharmaceutical composition is formulated as a suppository.

36. The pharmaceutical composition according to claim 23, 24 or 25, wherein the pharmaceutical composition is formulated for oral administration with an emulsifying agent.

37. The pharmaceutical composition according to claim 36, wherein the emulsifying agent is N-(4'-stearoylaminophenyl)-trimethylammonium methyl sulfuric acid.

38. The pharmaceutical composition according to claim 23, 24 or 25, wherein the clioquinol and vitamin $B_{12}$ are each purified.

39. The pharmaceutical composition of claim 34, wherein the clioquinol and vitamin $B_{12}$ are each purified.

40. A kit comprising in one or more containers an amount of clioquinol effective to treat or prevent Alzheimer's disease, and an amount of vitamin $B_{12}$ effective to inhibit a detrimental side effect of clioquinol administration.

* * * * *